United States Patent [19]

Kikuchi et al.

[11] Patent Number: 6,060,080
[45] Date of Patent: *May 9, 2000

[54] LIPOSOMAL PRODUCTS

[75] Inventors: Hiroshi Kikuchi; Kiyoto Yachi; Sadao Hirota, all of Tokyo, Japan

[73] Assignee: Daiichi Pharmaceutical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/409,924

[22] Filed: Mar. 23, 1995

Related U.S. Application Data

[63] Continuation of application No. 08/007,050, Jan. 21, 1993, abandoned, which is a continuation-in-part of application No. 07/729,266, Jul. 12, 1991, abandoned.

[30] Foreign Application Priority Data

Jul. 16, 1990 [JP] Japan ..................... 2-187370

[51] Int. Cl.[7] .................................................. A61K 9/127
[52] U.S. Cl. ................................ 424/450; 264/41; 264/43
[58] Field of Search ..................... 424/450, 1.21, 424/9.321, 9.51, 417; 264/4.1, 4.3; 436/829; 435/54

[56] References Cited

U.S. PATENT DOCUMENTS 4,310,506 1/1982 Baldeschwieler et al. ......... 424/450 X
4,756,910 7/1988 Yagi et al. ............................. 424/450
4,769,250 9/1988 Forssen ............................. 424/491 X
4,818,537 4/1989 Guo ...................................... 424/427
4,830,858 5/1989 Payne .................................... 424/450
4,873,088 10/1989 Mayhew ................................ 424/450
4,906,477 3/1990 Kurono et al. ......................... 424/450
4,927,571 5/1990 Huang et al. ....................... 424/450 X

FOREIGN PATENT DOCUMENTS 0219922 4/1987 European Pat. Off. .
0274174 7/1988 European Pat. Off. .
8203769 11/1982 WIPO .
8804573 6/1988 WIPO .

OTHER PUBLICATIONS

Grant & Hackh's Chemical dictionary. 1987. p. 205.

P. Buri et al. "Formes Pharmaceutiques Nouvelles", 1985, Technique et Documentation (Lavoisier), Paris FR, pp. 470 and 484.

Primary Examiner—Gollamudi S. Kishore
Attorney, Agent, or Firm—Sughrue, Mion, Zinn, Macpeak & Seas, PLLC

[57] ABSTRACT

A liposomal aqueous dispersion and method of making the liposomal aqueous dispersion is useful for encapsulation of drugs. The liposomal aqueous dispersion comprises: an aqueous suspension medium; multilamellar liposomes comprising an anionic phospholipid and cholesterol as essential components; neutral phospholipid in a mole ratio of 0 to 40% based on the total amount of said multilamellar liposomes; and a cation moiety-containing water-soluble drug, wherein the electrolyte concentration of said aqueous suspension medium is not more than 40 mM.

14 Claims, No Drawings

LIPOSOMAL PRODUCTS

This is a Continuation of application Ser. No. 08/007,050 filed Jan. 21, 1995, now abandoned, which is a Continuation-in-Part of application Ser. No. 07/729,266 filed Jul. 12, 1991 (abandoned).

FIELD OF THE INVENTION

This invention relates to liposomal products comprising a cation moiety-containing water-soluble drug and, as membrane components, an anionic phospholipid and cholesterol. The liposomal products according to the invention is superior in drug encapsulation efficiency, in stability in blood and, furthermore, in storage stability.

BACKGROUND OF THE INVENTION

Liposomes are widely used as models of biomembranes. Furthermore, they have recently been energetically investigated as a typical example of the drug delivery system (DDS).

However, when a water-soluble drug is encapsulated in liposomes by the conventional method, the encapsulation efficiency of drugs is generally low (in most cases 0.1 to 20%). There are two reasons: i) the mode of encapsulation of a low molecular weight water-soluble drug in liposomes basically consists distribution of the drug in the same concentration between the inner aqueous phase and outer aqueous phase of the liposomes and ii) for making liposomes stable as separate particles in an aqueous medium, it is necessarily required that the aqueous medium be present externally to liposomes as a dispersion medium therefor.

In view of the above, it has been considered very difficult to raise the drug encapsulation efficiency, in particular to a level close to 100%, when a water-soluble drug is caused to be encapsulated in liposomes.

Known methods for increasing the encapsulation efficiency of such a water-soluble drug or a drug having a small affinity for membranes include, among others, a) a reversed phase evaporation method (Proceedings of National Academy Sciences of U.S.A., 75, 4194, 1978), b) a chemical modification of drugs themselves (International Journal of Pharmaceutics, 14, 191, 1983; Journal of Pharmacobiodynamics, 7, 120, 1984; Chemical and Pharmaceutical Bulletin, 36, 3574, 1988), c) a use of other auxiliaries or the like (Journal of Pharmaceutical Sciences, 71, 958, 1982; Drug Development and Industrial Pharmacy, 10, 613, 1984), d) a modification of the properties of liposomal membranes themselves (Biochimica et Biophysica Acta, 812, 66, 1985; Biochimica et Biophysica Acta, 857, 123, 1986), and e) a use of a phospholipid having a charge opposite to the charge of the drug (Biochemical and Biophysical Research Communications, 107, 136, 1982; International Journal of Pharmaceutics, 17, 135, 1983; U.S. Pat. No. 4,769,250.

The prior art methods such as mentioned above are not satisfactory when a cation moiety-containing water-soluble drug is to be efficiently encapsulated in liposomes. In addition, when viewed as products for medical use, the liposomal products given by the prior art methods are quite unsatisfactory from the viewpoint of stability in blood.

SUMMARY OF THE INVENTION

As a result of extensive investigation to improve the above problems, it has been found that liposomal products comprising a cation moiety-containing water-soluble drug and, as membrane components, an anionic phospholipid and cholesterol is superior in drug encapsulation efficiency and also is very stable in blood or during storage. Based on the findings, the present invention has been completed.

Object of this invention is to provide liposomal products having a very high drug encapsulation efficiency and a very high stability in blood or during storage which can be produced with good reproducibility.

The above object of this invention can be accomplished by a liposomal products which comprises: a liposomal membrane comprising an anionic phospholipid and cholesterol as essential components; and a cation moiety-containing water-soluble drug whose encapsulation efficiency is very high.

DETAILED DESCRIPTION OF THE INVENTION

The anionic phospholipid to be used in the invention includes, among others, anionic phospholipids having saturated or unsaturated, straight or branched fatty acid residues containing about 10 to 30 carbon atoms, preferably saturated, straight or branched fatty acid residues containing about 14 to 16 carbon atoms and/or unsaturated, straight or branched fatty acid residues containing about 14 to 20 carbon atoms, such as phosphatidic acids and phsophatidylglycerols, more particularly dimyristoylphosphatidylglycerol, dipalmitoylphosphatidylglycerol, phosphatidylglycerols derived from naturally occurring substances such as egg yolk and soybean, completely hydrogenated phosphatidylglycerols, distearoylphosphatidyl-glycerol and the like. Preferred examples are dimyristoyl-phosphatidylglycerol, dipalmitoylphosphatidylglycerol, egg yolk-derived phosphatidylglycerol and the like. Dimyristoylphosphatidylglycerol is the most preferred. The anionic phospholipid is used generally in an amount of not less than 2, preferably 3 to 20 on the ionic equivalent basis relative to the used drug. Simply, the anionic phospholipid can be used in an amount of not less than 2 moles, preferably 3 to 20 moles per mole of the used drug.

Cholesterol, which is one of the liposomal membrane components to be used in accordance with the invention, is used generally in a mole percent of about 30 to 60%, preferably 40 to 55%, to the total amount of the membrane components used.

The liposomal membrane used in the invention may contain, in addition to the above-mentioned two components, a neutral phospholipid such as a phosphatidylcholine or sphingomyelin, and an antioxidant such as α-tocopherol. The neutral phospholipid mentioned above is generally used in a mole fraction of 0 to 40% preferably 0 to 35% and 0 to 30% and most preferably 0 to 20% based on the total amount of the membrane components used while the above-mentioned antioxidant is generally used in a mole percent of not more than about 5% on the same basis.

The aqueous medium in the liposomal products which is present inner and outer of the liposomes according to the invention is described below.

For assuring the stability of liposomes and drugs, the aqueous medium should generally have a pH of about 3 to 8. For the stability of liposomes, the pH should preferably be 6 to 8. Since the pH at which the drug is stable may differ drug by drug, the pH of the aqueous medium of the liposomal product according to the invention should suitably be determined within the pH range in which liposomes themselves are stable and in which the drug is stable. Thus, for instance, when such a drug as doxorubicin hydrochloride is used, the aqueous medium in the resulting liposomal product may have a pH of about 4.

Typical examples of the acid used for this pH adjustment include a monovalent inorganic acid such as hydrochloric acid, nitric acid or hydrobromic acid, or a monovalent organic acid such as lactic acid, glyceric acid or acetic acid. Hydrochloric acid and lactic acid are preferred, however. The base for such pH adjustment includes monovalent hydroxides such as potassium hydroxide, sodium hydroxide and lithium hydroxide, and monovalent amines such as triethylamine, trimethylamine, diisopropanolamine, diethanolamine, triethanolmaine, tetramethylamine and tris (hydroxymethyl)aminomethane. Among these, potassium hydroxide and sodium hydroxide are preferred. Furthermore, acids containing a divalent or trivalent ion, such as potassium primary phosphate, sodium secondary phosphate and sodium carbonate, may also be used.

The electrolyte ion concentration in the aqueous medium should desirably be as low as possible and, generally, the total concentration of ions except the drug should suitably be not more than about 40 mM. An anionic phospholipid usually can be obtained in the form of sodium or calcium salt. Therefore, the amount of the electrolyte derived therefrom must be taken into account.

The osmotic pressure of the aqueous medium preferably be equal or close to that of body fluids. Preferred isotonizing agents to be used therefor include polyhydric alcohols such as glycerol and propylene glycol, and saccharides such as mannitol, sucrose, glucose and lactose.

The liposomes suited for use in this invention are now described below in detail.

From the viewpoint of stability in blood, the liposomes should generally have a particle size of about 50 to 1,000 nm, preferably 60 to 300 nm, more preferably 70 to 200 nm. For sizing of liposomes to attain such a particle size, techniques in general use may be employed, for example emulsification treatment using an ultrasonicator, or extrusion treatment through a polycarbonate membrane filter under high pressure. From the stability-in-blood viewpoint, it is desirable that the liposomes according to the invention have a plurality of membranes. The number of membranes is not limited to any particular value or range. Such liposomes can be produced by suitably using such a conventional sizing technique as mentioned above, in particular the extrusion technique.

The term "cation moiety-containing water-soluble drug" as used herein means a water-soluble drug forming a cation in aqueous solution (neutral pH region) and includes, as typical examples thereof, anthracycline antitumor agents such as doxorubicin hydrochloride, daunorubicin hydrochloride, epirubicin and pirarubicin, and antimicrobial agents such as gentamicin and nystatin, among others.

The process for preparing of the liposomal products according to this invention is described below.

According to the various known methods, for example the method disclosed in Journal of Molecular Biology, 13, 238 (1965), the liposomal membrane components mentioned above are first dissolved in an appropriate organic solvent, such as chloroform or methanol, and then the solvent is distilled off to cause formation of a lipid film. From the efficiency viewpoint, it is advantageous that the drug such as mentioned above be admixed in advance with the membrane components, although the drug may also be dissolved in advance in the aqueous medium to be added later. To the lipid film aqueous medium is added in a low electrolyte concentration such that the total concentration of ion except the drug is not more than 40 mM, and preferably not more than 20 mM, to thereby cause hydration and swelling. Dispersion is further effected using a mixer such as a vortex mixer or an agitating/homogenizing mixer to give a crude liposomal dispersion. In this step, when the temperature of the aqueous medium is higher, a higher emulsification efficiency will be obtained. However, when the temperature is extremely high, the drug may be decomposed in certain instances. Caution is needed accordingly. Generally, a temperature within the range of 50° to 70° C. can preferably be used. The aqueous medium to be added in this step may contain a buffer, such as phosphoric acid or lactic acid. The electrolyte ion concentration in the medium should be not more than 40 mM in total except the drug, as mentioned above, and the pH should suitably be selected generally within the range of 3 to 8. When doxorubicin hydrochloride, for instance, is used as the drug, the pH should be adjusted to about 4 and a polyhydric alcohol or a saccharide may be added as an isotonizing agent, as mentioned above. In this step, such crude liposomal dispersion may be produced by any other known method for preparation of liposomes (e.g. Annual Review of Biophysics and Engineering, 9, 467, 1980; JP-A-60-7932, JP-A-60-7933, JP-A-60-7934, JP-A-60-12127 and JP-A-62-152531, "JP-A" as used herein means an "unexamined published Japanese patent application").

Since the thus-obtained crude dispersion generally has a liposome particle size of about 1 μm, the dispersion may, as desired, be converted to a homogenized liposomal dispersion with a smaller particle size in a step of sizing. The sizing may be effected, as mentioned above, by emulsifying treatment using an ultrasonicator, a Manton-Gaulin homogenizer, a microfluidizer or the like homogenizing mixer and/or extrusion treatment under high pressure through a polycarbonate membrane filter with a certain specified pore size.

With the liposomal membrane formulation in accordance with the invention, liposomes having a particle size of 50 to 200 nm can generally be obtained with a desired number of membranes by passing the crude liposomal dispersion once or twice through a polycarbonate membrane filter having a pore size of 0.2 μm under high pressure. In this step almost no residue remains on the filter. The fact that the liposomes obtained have a plurality of membranes can be confirmed by observation under an electron microscope and on the basis of an estimated value derived from the encapsulation volume, L (liters)/M (mole), as determined for a water-soluble model drug and the particle size. More preferably, the crude dispersion should be passed once through a filter with a large pore size (e.g. 0.6 μm) prior to the passage through a filter with a pore size of 0.2 μm so that larger-size particles can preliminarily be sized and foreign materials and insoluble materials can be removed in advance. In the above sizing step, a higher efficiency can generally be obtained when the temperature of the aqueous medium is higher. At an extremely high temperature, however, the drug may be decomposed chemically. A temperature between 50° and 70° C. is generally preferable and appropriate.

The thus-obtained liposomal dispersion is submitted to the final preparation step. The pH may be readjusted in advance to a desired level using a low concentration aqueous solution of sodium hydroxide or potassium hydroxide or the like such as mentioned above. It goes without saying that the total electrolyte ion concentration (except the drug) should desirably be 40 mM or below. The final step is generally started with bacterial filtration. More specifically, the aqueous dispersion of liposomes as obtained in the above manner is passed through a membrane filter with a pore size of 0.4 µm to 0.2 µm. Then, when the liposomal products according to the invention are in the form of an aqueous dispersion, the filtrate is distributed as such in portions as desired into ampules or other containers, which are then sealed. When a frozen preparation is desired, the contents in the sealed containers are frozen at −5° to −80° C., preferably −30° to −40° C. Furthermore, when a lyophilized preparation is desired, the filtrate is distributed into vials or other containers and then subjected to lyophilization in a conventional manner. Desirable lyophilization conditions are as follows: rapid freezing should be attained at a freezing temperature of −5° to −80° C., preferably −30° to −40° C. and water should be sublimed at a reduced pressure of 0.1 torr or below. Finally, when a spray-dried preparation is desired, the above-mentioned aqueous liposomal dispersion is spray-dried for solvent removal and the powder obtained is distributed under aseptic conditions into vials or other appropriate containers, which are then sealed. Spray-drying conditions which are desirable include an inlet temperature of 110° to 200° C., preferably 120° to 150° C.

The present invention makes it possible to produce liposomal products with a very high drug encapsulation efficiency and with good reproducibility. Furthermore, the liposomal products according to the invention are highly stable in the blood and, in addition, are excellent in liposome stability and drug encapsulation efficiency during storage irrespective of whether they are aqueous dispersion preparations or lyophilized preparations. Thus, the invention provides very excellent liposomal products.

The present invention is now illustrated in greater detail by way of the following examples, but it should be understood that the present invention is not deemed to be limited thereto. The preparative procedures, analytical methods and so forth which are identical throughout the examples are first described in the following. The charged lipids used in examples 1 to 20 were sodium salts. Those used in Examples 21 and 22 were in the free state.

Procedures for Producing Crude Dispersions of Liposomes

1. Organic Solvent Method A:
   The lipid membrane components and doxorubicin hydrochloride were placed in a glass container and once completely dissolved in a mixture of chloroform and methanol. The organic solvents were then distilled off under a nitrogen gas stream or under reduced pressure, followed by further drying in a desiccator (under reduced pressure). A lactate buffer (9 mM) isotonized substantially to the biological osmotic pressure was then added thereto, and the whole was agitated with a vortex mixer or agitating/homogenizing mixer with gentle warming to give a crude dispersion of liposomes.
2. Organic Solvent Method B:
   The lipid membrane components were placed in a glass container and once completely dissolved in a mixture of chloroform and methanol. The organic solvents were then distilled off under a nitrogen gas stream or under reduced pressure, followed by further drying in a desiccator (under reduced pressure). Then, a solution of doxorubicin hydrochloride in the above-mentioned buffer substantially isotonic to the biological osmotic pressure or a buffer containing 10% sucrose was added thereto, and the whole was agitated with a vortex mixer or agitating/homogenizing mixer with gentle warming to give a crude dispersion of liposomes.
3. Polyhydric Alcohol Method:
   A necessary amount of glycerol was placed in a glass container and heated. The lipid membrane components were then swelled and dissolved in the glycerol. The resultant solution was cooled to 50° to 70° C. and a concentrated aqueous solution of doxorubicin hydrochloride was added thereto. The whole was kneaded and mixed up. To this mixture was added a solution of sugar in the above-mentioned buffer, followed by agitation with an agitating/homogenizing mixer at 50° to 70° C. The osmotic pressure of the final aqueous medium was adjusted to render it substantially identical to the biological osmotic pressure.

Procedures for Producing Liposomal Dispersions

1. Ultrasonic Method A:
   The tip of a tip-type ultrasonicator was inserted into the container containing the crude liposomal dispersion and emulsification was carried out to give an aqueous liposomal dispersion with a liposome particle size of 50 nm or less.
2. Ultrasonic Method B:
   The tip of a tip-type ultrasonicator was inserted into the container containing the crude liposomal dispersion and emulsification was carried out to give an aqueous liposomal dispersion with a liposome particle size of 50 to 200 nm.
3. Microfluidizer Method A:
   The crude liposomal dispersion was treated in a microfluidizer for emulsification, to give an aqueous liposomal dispersion with a liposome particle size of 50 nm or less.
4. Microfluidizer Method B:
   The crude liposomal dispersion was treated in a microfluidizer for emulsification, to give an aqueous liposomal dispersion with a liposome particle size of 50 to 200 nm.
5. Extrusion Method A:
   The crude liposomal dispersion was subjected to high pressure filtration through a polycarbonate membrane filter with a pore size of 0.05 µm to give an aqueous liposomal dispersion with a liposome particle size of 50 nm or less.
6. Extrusion Method B:
   The crude liposomal dispersion was subjected to high pressure filtration through a polycarbonate membrane filter with a pore size of 0.2 µm to give an aqueous liposomal dispersion with a particle size of 50 to 200 nm.

Analytical Methods

1. Particle Size and Number of Membranes:
   For each aqueous dispersion of liposomes containing doxorubicin hydrochloride and for an aqueous liposomal dispersion reconstituted from each lyophilized liposomal preparation, liposome particle size determination was performed by the quasi-elastic light scattering method. That the liposomes obtained in each example has a plurality of membranes was confirmed by means of an electron microscope and on the basis of an estimated value derived from the encapsulation volume (L/M) determined with a water-soluble model drug and the particle size.
2. Encapsulation Efficiency of Drug:
   For each aqueous dispersion of doxorubicin hydrochloride-containing liposomes and for an aqueous liposomal dispersion reconstituted from each lyophilized liposomal preparation, the encapsulation efficiency of doxorubicin hydrochloride in liposomes was determined by the ultracentrifugation method.

Table 3 shows the electrolyte concentration used in Examples 1 to 22. From the data in Tables 1, 2, 3, 4 and 5, it can be seen that when the electrolyte concentration is less than 40 mM, particularly less than 20 mM, the encapsulation efficiency is unexpectedly high.

3. Stability in Blood:

The aqueous liposomal dispersion (1.5 ml) reconstituted from doxorubicin hydrochloride-containing lyophilized liposomes was added to 5.8 ml of a rat serum and, after an hour of incubation at 37° C., the encapsulation efficiency of doxorubicin hydrochloride in liposomes was determined in the same manner as mentioned above.

As shown in Table 1, it was confirmed that, in the final liposomal products according to the invention, 90% or more (nearly to 100%) of doxorubicin hydrochloride can be encapsulated in liposomes and the final products are stable in the blood.

The liposomes of Example 3 were evaluated for antitumor activity. They were comparable to free doxorubicin hydrochloride in in vitro cell proliferation inhibiting effect (tumor cells: P388 mouse leukemia cells, QG56 human lung squamous cell carcinoma cells, HOC21 human ovarian cancer cells, and MKN-28 human stomach cancer cells) as well as in in vivo antitumor effect (MH-134 cancer-bearing mice).

The liposomes of Example 3 were subjected to safety testing in rats. Electrocardiography, clinical symptom observation, blood chemistry and other tests revealed that the liposomes were evidently lower in cardiotoxicity, alopecia incidence rate, diarrhea incidence rate, hemotoxicity and so on as compared with free doxorubicin hydrochloride.

As mentioned above, it has become evident that the doxorubicin hydrochloride-containing liposomal products, which is one embodiment of the present invention, can retain 90% or more of the doxorubicin hydrochloride added with good reproducibility, has very high stability in the blood and can reduce various toxicities intrinsic of doxorubicin hydrochloride.

The raw material used in Examples 1 to 22 is shown below:

RAW MATERIAL OF ANIONIC PHOSPHOLIPID IN EXAMPLES (1) Examples 1–11, 13, 14, 17, 19 and 20

DMPG: L-α-dimyristoylphosphatidyl-DL-glycerol (trade name: MGLS-4040, manufactured by Nippon Oil & Fats Co., Ltd.)

(2) Example 12

DPPG: L-α-dipalmitoylphosphatidyl-DL-glycerol (trade name: MGLS-6060, manufactured by Nippon Oil & Fats Co., Ltd.)

(3) Examples 15 and 18

DSPG: L-α-distearoylphosphatidyl-DL-glycerol (trade name: MGLS-8080, manufactured by Nippon Oil & Fats Co., Ltd.)

(4) Example 16

Hydrogenated PG: Hydrogenated phosphatidylglycerol (manufactured by Asahi Chemical Industry Co., Ltd.) There is no particular trade name.

(5) Examples 21 and 22

DMPG: L-α-dimyristoylphosphatidylglycerol (trade name: PhosphoLipid-DMPG, manufactured by Nippon Fine Chemical Co., Ltd.)

TABLE 1

| | Amounts of Membrane Components per 1.29 mM of Doxorubicin Hydrochloride, mM (mole ratio to active ingredient) | | | Aqueous Medium | | | Preparation of Crude Dispersion | Sizing | Particle Size (nm) | | Encapsulation Efficiency of Active Ingredient (%) | | Stability in blood (%) |
|---|---|---|---|---|---|---|---|---|---|---|---|---|---|
| Example No. | Charged Lipid | Cholesterol | Other | Solutes | pH | Scale (ml) | | | Before Lyophilization | After Lyophilization | Before Lyophilization | After Lyophilization | |
| Example 1 | DMPG 11.4 (8.8) | 14(10.9) | eggPC 4 (3.1) | Sucrose-lactic acid | 4.0 | 10 | Organic solvent method A | Extrusion B | 81 | 103 | 100.0 | 99.9 | 89.1 |
| Example 2 | DMPG 11.4 (8.8) | 12(9.3) | eggPC 2 (1.6) | Sucrose-lactic acid | 4.0 | 2 | Polyhydric alcohol | Extrusion B | 125 | 130 | 100.0 | 100.0 | 95.2 |
| Example 3 | DMPG 11.4 (8.8) | 12(9.3) | eggPC 2 (1.6) | Sucrose-lactic acid | 4.0 | 20 | Organic solvent method A | Extrusion B | 91 | 90 | 99.9 | 99.9 | 91.4 |
| Example 4 | DMPG 11.4 (8.8) | 12(9.3) | eggPC 2 (1.6) | Sucrose-lactic acid | 4.0 | 20 | Organic solvent method B | Extrusion B | 85 | 93 | 99.8 | 99.9 | 88.4 |
| Example 5 | DMPG 11.4 (8.8) | 12(9.3) | eggPC 2 (1.6) | Sucrose-lactic acid | 4.0 | 20 | Organic solvent method A | Ultrasonic B | 156 | 178 | 99.7 | 100.0 | 86.5 |
| Example 6 | DMPG 11.4 (8.8) | 12(9.3) | eggPC 2 (1.6) | Sucrose-lactic acid | 4.0 | 20 | Organic solvent method A | Microfluidizer B | 190 | 173 | 100.0 | 99.8 | 92.0 |
| Example 7 | DPPC 11.4 (8.8) | 12(9.3) | eggPC 2 (1.6) | Sucrose-lactic acid | 4.0 | 10 | Organic solvent method A | Extrusion B | 75 | 98 | 99.7 | 99.8 | 82.4 |
| Example 8 | DMPG 11.4 (8.8) | 10(7.8) | eggPC 2 (1.6) | Sucrose-lactic acid | 4.0 | 20 | Organic solvent method A | Extrusion B | 95 | 90 | 99.9 | 99.9 | 86.8 |
| Example 9 | DMPG 10 (7.8) | | 10(7.8) | Sucrose-lactic acid | 4.0 | 10 | Organic solvent method A | Extrusion B | 120 | 111 | 100.0 | 99.7 | 82.2 |
| Example 10 | DMPG 8 (6.2) | 10(7.8) | eggPC 2 (1.6) | Sucrose-lactic acid | 4.0 | 10 | Organic solvent method A | Extrusion B | 132 | 129 | 99.8 | 100.0 | 88.0 |
| Example 11 | DMPG 6 (4.7) | 10(7.8) | eggPC 4 (3.1) | Sucrose-lactic acid | 4.0 | 10 | Organic solvent method A | Extrusion B | 110 | 107 | 100.0 | 99.6 | 80.2 |
| Example 12 | DPPG 6 (4.7) | 10(7.8) | eggPC 4 (3.1) | Sucrose-lactic acid | 4.0 | 10 | Organic solvent method A | Extrusion B | 100 | 95 | 99.6 | 99.5 | 82.0 |
| Example 13 | DMPG 4 (3.1) | 10(7.8) | eggPC 6 (4.7) | Sucrose-lactic acid | 4.0 | 10 | Organic solvent method A | Extrusion B | 98 | 105 | 99.9 | 99.7 | 84.4 |

TABLE 1-continued

| Example No. | Amounts of Membrane Components per 1.29 mM of Doxorubicin Hydrochloride, mM (mole ratio to active ingredient) | | | Aqueous Medium | | Scale (ml) | Preparation of Crude Dispersion | Sizing | Particle Size (nm) | | Encapsulation Efficiency of Active Ingredient (%) | | Stability in blood (%) |
|---|---|---|---|---|---|---|---|---|---|---|---|---|---|
| | Charged Lipid | Cholesterol | Other | Solutes | pH | | | | Before Lyophilization | After Lyophilization | Before Lyophilization | After Lyophilization | |
| Example 14 | DMPG 3 (2.3) | 10(7.8) | eggPC 7 (5.4) | Sucrose-lactic acid | 4.0 | 10 | Organic solvent method A | Extrusion B | 95 | 99 | 99.5 | 99.6 | 80.5 |
| Example 15 | DSPG 11.4 (8.8) | 12(9.3) | eggPC 2 (1.6) | Sucrose-lactic acid | 4.0 | 10 | Organic solvent method A | Extrusion B | 170 | 195 | 90.7 | 90.3 | 77.4 |
| Example 16 | Hydrogenated PG 11.4 (8.8) | 12(9.3) | eggPC 2 (1.6) | Sucrose-lactic acid | 4.0 | 20 | Organic solvent method A | Extrusion B | 167 | 200 | 91.0 | 90.4 | 75.3 |
| Example 17 | DMPG 11.4 (8.8) | 8(6.2) | eggPC 2 (1.6) | Sucrose-lactic acid | 4.0 | 20 | Organic solvent method A | Extrusion B | 99 | 103 | 99.7 | 99.8 | 70.7 |
| Example 18 | DSPG 5.2 (4.0) | 7.7(6.0) | DSPC 6.5 (5.0) | 10% Aqueous solution of sucrose | 7.4 | 20 | Organic solvent method A | Ultrasonic A | 45 | 248 | 87.3 | 88.1 | 64.4 |
| Example 19 | DMPG 11.4 (8.8) | 12(9.3) | eggPC 2 (1.6) | Sucrose-lactic acid | 4.0 | 20 | Organic solvent method A | Extrusion A | 44 | 425 | 99.9 | 99.7 | 57.2 |
| Example 20 | DMPG 11.4 (8.8) | 12(9.3) | eggPC 2 (1.6) | Sucrose-lactic acid | 4.0 | 20 | Organic solvent method A | Ultrasonic A | 49 | 223 | — | 99.9 | 60.3 |

Note 1:
DMPG: sodium salt of Dimyristoylphosphatidylglycerol,
DPPG: sodium salt of Dipalmitoylphosphatidylglycerol,
DSPG: sodium salt of Distearoylphosphatidylglycerol,
Hydrogenated PG: Hydrogenated phosphatidylglycerol,
eggPC: sodium salt of Egg yolk-derived phosphatidylcholine,
DSPC: Distearoylphosphatidylcholine.
Note 2:
Sucrose-lactic acid: 9 mM lactate buffer supplemented with 9% sucrose.

TABLE 2

| Example No. | Amounts of Membrane Components, mM (mol ratio to active ingredient) | | | Aqueous Medium | | Scale (ml) | Preparation of Crude Dispersion | Sizing | Particle Size (nm) | | Encapsulation Efficiency of Active Ingredient (%) | | Stability in blood (%) |
|---|---|---|---|---|---|---|---|---|---|---|---|---|---|
| | Charged Lipid | Cholesterol | Active Ingredient | Solutes | pH | | | | Before Lyophilization | After Lyophilization | Before Lyophilization | After Lyophilization | |
| Example 21 | DMPG 52 (8.1) | 48 (7.5) | AMK 6.40 | 10% sucrose | — | 150 | Organic solvent method B | Extrusion B | — | 146 | — | 99.9 | 91.5 |
| Example 22 | DMPG 52 (15.2) | 48 (14.0) | SM 3.43 | 10% sucrose | — | 150 | Organic solvent method B | Extrusion B | — | 131 | — | 98.8 | 88.7 |

Note 3:
AMK: Amikacin sulfate.
SM: Streptomycin sulfate.

TABLE 3

Total Electrolyte Concentration in Examples 1 to 22.

| Example No. | Concentration of Electrolytes | Anionic Phospholipid |
|---|---|---|
| Example 1 | 16mM | DMPG |
| Example 2 | 16mM | DMPG |
| Example 3 | 16mM | DMPG |
| Example 4 | 16mM | DMPG |
| Example 5 | 16mM | DMPG |
| Example 6 | 16mM | DMPG |
| Example 7 | 16mM | DMPG |
| Example 8 | 16mM | DMPG |
| Example 9 | 15mM | DMPG |
| Example 10 | 13mM | DMPG |
| Example 11 | 11mM | DMPG |
| Example 12 | 11mM | DMPG |
| Example 13 | 9mM | DMPG |
| Example 14 | 8mM | DMPG |
| Example 15 | 16mM | DSPG |
| Example 16 | 16mM | H-PG |
| Example 17 | 16mM | DMPG |
| Example 18 | 10mM | DSPG |
| Example 19 | 15mM | DMPG |
| Example 20 | 16mM | DMPG |
| Example 21 | 0mM | DMPG |
| Example 22 | 0mM | DMPG |

TABLE 4

Effect of Concentration of Electrolytes on Encapsulation Efficiency of Doxorubicin [ADM] into Liposomes

| Concentration of electrolytes | Molar ratio (DMPG/ADM[2]) | Appearance[3] | Encapsulation efficiency (%) |
|---|---|---|---|
| 15mM | 8.7 | good | 99.6 |
| 42mM | 8.7 | good | 97.6 |
| 69mM | 8.7 | good | 95.5 |
| 96mM | 8.7 | good | 94.4 |
| 123mM | 8.7 | good | 92.7 |
| 150mM | 8.7 | good | 90.4 |
| 177mM | 8.7 | good | 86.2 |
| 204mM | 8.7 | good | 84.5 |
| 231mM | 8.7 | good | 82.8 |
| 258mM | 8.7 | good | 81.3 |
| 285mM | 8.7 | good | 80.5 |

[1]Dimyristoylphosphatidylglycerol [DMPG]/Egg yolk phosphatidylcholine [Egg/PC]/Cholesterol [Chol] = 15 mM/2.7 mM/16 mM.
[2]Concentration of ADM = 1.0 mg/ml (1.72 mM).
[3]Particle size was not determined.

TABLE 5

Effect of Concentration of Electrolytes on Encapsulation Efficiency of Doxorubicin [ADM] into Liposomes[1] II

| Concentration of electrolytes | Molar ratio (DMPG/ADM[2]) | Appearance[3] | Encapsulation efficiency (%) |
|---|---|---|---|
| 26 mM | 15.1 | good | 98.7 |
| 41 mM | 15.1 | good | 97.9 |
| 56 mM | 15.1 | good | 97.2 |
| 71 mM | 15.1 | good | 96.3 |
| 86 mM | 15.1 | good | 96.1 |
| 116 mM | 15.1 | good | 96.0 |
| 146 mM | 15.1 | good | 95.4 |
| 176 mM | 15.1 | good | 94.5 |
| 221 mM | 15.1 | good | 94.0 |
| 266 mM | 15.1 | good | 93.4 |
| 296 mM | 15.1 | good | 92.5 |
| 326 mM | 15.1 | good | 91.9 |

[1]Dimyristoylphosphatidylglycerol [DMPG]/Cholesterol [Chol] = 26 mM/24 mM.
[2]Concentration of ADM = 1.0 mg/ml (1.72 mM).
[3]Particle size was not determined.

Also, Table 2 shows the results of the case of other drugs than doxorubicin hydrochloride, that is, amikacin sulfate and streptomycin sulfate. Similar to doxorubicin hydrochloride, these drugs which have cation moieties can be encapsulated with a very high encapsulation efficiency in the liposomal products according to the invention. In addition, these liposomal products are very highly stable in the blood.

While the invention has been described in detail and with reference to specific embodiments thereof, it will be apparent to one skilled in the art that various changes and modifications can be made therein without departing from the spirit and scope thereof.

What is claimed is:

1. An aqueous liposomal dispersion which comprises:
   (1) an aqueous suspension medium;

(2) a water-soluble cationic drug encapsulated in multilamellar liposomes having membranes made of membrane material comprising:
  (a) an anionic phospholipid comprised of saturated fatty acid residues having 10 to 30 carbon atoms, and
  (b) cholesterol, and,
  (c) a neutral phospholipid,
wherein the mole ratio of said cholesterol is 30 to 60% of the total amount of all membrane material and the mole ratio of said neutral phospholipid is 0 to 40% of the total amount of all membrane material; and wherein:
  (1) the total electrolyte concentration of said aqueous suspension medium not including the drug used is not more than 40 mM; and
  (2) said anionic phospholipid is present in an amount of not less than 2 on an ionic equivalent basis relative to the amount of the drug.

2. A method of producing an aqueous liposomal dispersion in an aqueous suspension medium and containing a water-soluble cationic drug, said method comprising admixing said aqueous suspension medium with:
  (1) a lipid film of membrane material comprising:
    (a) an anionic phospholipid comprised of saturated fatty acid residues having 10 to 30 carbon atoms,
    (b) cholesterol, and,
    (c) a neutral phospholipid,
  wherein the mole ratio of said cholesterol is 30 to 60% of the total amount of all membrane material, and the mole ratio of neutral phospholipid is 0 to 40% of the total amount of all membrane material; and
  (2) a water-soluble cationic drug;
  wherein said drug is present in either the aqueous suspension medium or the lipid film; and
whereby multilamellar liposomes containing the drug are formed in the aqueous suspension medium; and wherein:
  (A) the total electrolyte concentration of said aqueous suspension medium not including the drug used is not more than 40 mM; and
  (B) said anionic phospholipid is present in an amount of not less than 2 on an ionic equivalent basis relative to the drug.

3. A method of improving the encapsulation efficiency of a water-soluble cationic drug in liposomes, said method comprising admixing said aqueous suspension medium with:
  (1) a lipid film of membrane material comprising:
    (a) an anionic phospholipid comprised of saturated fatty acid residues having 10 to 30 carbon atoms,
    (b) cholesterol, and,
    (c) a neutral phospholipid,
  wherein the mole ratio of said cholesterol is 30 to 60% of the total amount of all membrane material, and the mole ratio of neutral phospholipid is 0 to 40% of the total amount of all membrane material; and
  (2) a water-soluble cationic drug; wherein said drug is present in either the aqueous suspension medium or the lipid film; and
whereby multilamellar liposomes containing the drug are formed in the aqueous suspension medium; and wherein:
  (A) the total electrolyte concentration of said aqueous suspension medium not including the drug used is not more than 40 mM; and
  (B) said anionic phospholipid is present in an amount of not less than 2 on an ionic equivalent basis relative to the drug.

4. The aqueous liposomal dispersion as claimed in claim 1, wherein said liposomes have a particle size of 50 to 1,000 nm.

5. The aqueous liposomal dispersion as claimed in claim 1, wherein said membranes comprise an anionic phospholipid, cholesterol and a neutral phospholipid.

6. The aqueous liposomal dispersion as claimed in claim 1, wherein the anionic phospholipid is present in an amount of 3 to 20 on an ionic equivalent basis relative to the amount of drug.

7. The aqueous liposomal dispersion as claimed in claim 1, wherein the anionic phospholipid is comprised of saturated fatty acid residues having 14 to 16 carbon atoms.

8. A liposomal product prepared by spray-drying the aqueous liposomal dispersion as claimed in claim 1.

9. A liposomal product prepared by lyophilizing the aqueous liposomal dispersion as claimed in claim 1.

10. A liposomal product prepared by freezing the aqueous liposomal dispersion as claimed in claim 1.

11. The method of producing an aqueous liposomal dispersion as claimed in claim 2, wherein the anionic phospholipid is present in an amount of 3 to 20 on an ionic equivalent basis relative to the amount of drug.

12. The method of producing an aqueous liposomal dispersion as claimed in claim 2, wherein the anionic phospholipid is comprised of saturated fatty acid residues having 14 to 16 carbon atoms.

13. The method of improving the encapsulation efficiency of a water-soluble cationic drug in liposomes as claimed in claim 3, wherein the anionic phospholipid is present in an amount of 3 to 20 on an ionic equivalent basis relative to the amount of drug.

14. The method of improving the encapsulation efficiency of a water-soluble cationic drug in liposomes as claimed in claim 3, wherein the anionic phospholipid is comprised of saturated fatty acid residues having 14 to 16 carbon atoms.

* * * * *